United States Patent [19]

O'Lenick, Jr.

[11] Patent Number: 5,164,471

[45] Date of Patent: Nov. 17, 1992

[54] FLUORINE CONTAINING SILANOL POLYESTER WAXES

[75] Inventor: Anthony J. O'Lenick, Jr., Lilburn, Ga.

[73] Assignee: Siltech Inc., Norcross, Ga.

[21] Appl. No.: 837,152

[22] Filed: Feb. 19, 1992

[51] Int. Cl.$^5$ ............................................. C08G 77/04
[52] U.S. Cl. ........................................ 528/26; 528/42; 528/25; 528/29; 525/474; 525/446
[58] Field of Search ............... 528/26, 42, 25, 29; 525/446, 474

[56] References Cited

U.S. PATENT DOCUMENTS

| | | | |
|---|---|---|---|
| 3,038,000 | 6/1962 | Schmidt | 528/42 |
| 4,812,518 | 3/1989 | Haubennestel et al. | 525/100 |
| 4,937,277 | 6/1990 | O'Lenick, Jr. | 524/318 |
| 5,051,489 | 9/1991 | O'Lenick, Jr. | 528/26 |

Primary Examiner—Melvyn I. Marquis
Assistant Examiner—Margaret W. Glass

[57] ABSTRACT

The invention discloses novel fluorine containing silanol polyester waxes. Compounds of the invention by virtue of (a) the polyester group, and (b) the fluorine containing terminal groups are extremely efficient lubricating materials when applied to a variety of surfaces. These materials spread out when applied and provide durable lubrication and hydrophobicity when applied to hair, skin, wood, plastic and textile fibers. The compounds of the present invention are prepared by reacting a silanol compound with a dicarboxylic acid and a fluorine containing alcohol.

16 Claims, No Drawings

5,164,471

FLUORINE CONTAINING SILANOL POLYESTER WAXES

BACKGROUND OF THE INVENTION

1. Field of the Invention

The present invention relates to a series of novel fluorine containing silanol polyesters which provide outstanding lubrication, and hydrophobicity to a variety of surfaces. The compounds of the invention are waxy solids which melt under pressure to give a clear liquid lubricating oil. The esterification by which the compounds are prepared is the reaction of a silanol, a hydroxy containing silicone polymer, a dicarboxylic acid and a fluorine containing alcohol. In the instance where the fluorine containing alcohol contains only one hydroxyl group, it will become a terminal group in the polyester.

2. Arts and Practices

Silicone compounds have been known to be active at the surface of plastic, cellulosic and synthetic fibers as well as paper. They are good nondurable lubricants and are very stable to oxidation, however, their high cost and lack of efficiency at low concentrations as well as low durability have made their acceptance in commercial products quite low. In all instances, commercially available quaternaries are the active ingredient in traditional laundry care markets, with little or no silicone added.

The low efficiency and low durability of dimethylpolysiloxane is due to the fact that it is very water insoluble and deposits on the surface to obtain a minimum free energy in the solution. Simply, the silicone oil delivery to the surface by hydrophobic binding, not chemical bonding. At the surface, the dimethylpolysiloxane is a very effective fiber lubricant, however, there are two drawbacks, first; the dimethylpolysiloxane is not chemically bonded so the effect is very transient and disappears with one washing, and second; since there is no reaction of the dimethylpolysiloxane to the surface an equilibrium between fiber absorbed dimethylpolysiloxane and dimethylpolysiloxane in the dispersion results in very inefficient percentage of silicone deposited. A large amount of the expensive silicone goes down the drain with the waste water.

In many applications, there is a strong desire to obtain a solid wax which can be used in applications were a spread on application is of interest. These applications include personal care applications like antiperspirants and skin creams. Unfortunately most silicone derivatives are liquid to very low temperatures. Attempts ot overcome this deficiency have been made by reacting stearyl alcohol with a chloro silane. The difficulty with the use of this type of material is that a large excess (50% by weight) of the alcohol needs to be added to get a product which is free of the irritating chlorosilane raw material. When such an excess is used the product behaves functionally more like the stearyl alcohol than like a silicone compound. Additionally, the compound is not polymeric, hence the superior lubrication and hydrophobicity enhancements which can be achieved by dimethylpolysiloxane is not obtainable with these compounds.

U.S. Pat. No. 3,511,699 to Sterman issued May 12, 1970 teaches that epoxy compounds placed in the silicone backbone by hydrosilation can be cured onto certain fibers to give improved substantivity. The substantivity is based upon the reaction of hydroxyl groups on the cellulosic and the epoxy group in the silicone polymer. The resulting bond is a ether linkage and a new hydroxyl group. While a definite improvement over other compounds the efficiency and durability of the were not good enough to allow for cost effective incorporation of these materials in detergent formulations.

U.S. Pat. No. 5,051,489 issued to O'Lenick, Jr. teaches that silicone esters can be prepared by the reaction of silanols and fatty acids. These compounds lack the critical flourine containing component.

THE INVENTION

OBJECT OF THE INVENTION

It is the object of the present invention to provide novel fluorine containing silanol polyester compound which is very lubricious and spreads out into a very thin durable film on a variety of surfaces. These waxes are substantive to the surface of a fibrous, plastic or cellulosic material, providing lubrication and hydrophobicity at very low concentrations.

It is another objective of the current invention to provide fluorine containing silanol polyesters which can be used in textile, and personal care applications to render softness and lubrication to the substrates being treated. The superior antistatic properties are an important benefit, since this is a major aspect of consumer perception of softness in consumer and industrial laundry applications. Lubrication has been a property which is purported to effect garment life. Application of the compounds of the invention can be from solvent, aqueous dispersion or solution, or applied neat in these processes. The compounds of the current invention make outstanding napping lubricants since a waxy material which liquefies under application of pressure is desirable in this application. The incorporation of fluorine into the polyester results in the spreadability and the ability to use these materials at heretofore unknown concentrations and still obtain efficacy.

SUMMARY OF THE INVENTION

The present invention relates to novel fluorine containing silanol polyester compounds. Compounds of the invention by virtue of (a) the polyester group, and (b) the fluorine containing terminal groups are extremely efficient lubricating materials when applied to a variety of surfaces. These materials spread out when applied and provide durable lubrication and hydrophobicity when applied to hair, skin, wood, plastic and textile fibers. The compounds of the present invention are prepared by reacting a silanol compound with a polycarboxylic acid and a fluorine containing alcohol. The compounds of this invention are fluorine containing silanol polyesters made by the esterification of a dicarboxylic acid, ester or anhydride, a silanol compound and a fluorine containing alcohol. Specifically, the compounds of the present invention are fluorine containing silanol polyester compound which is prepared by the esterification reaction of;

(a) a silanol compound conforming to the following structure;

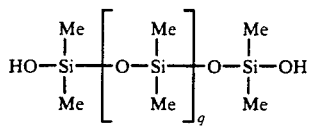

q is an integer ranging from 1 to 2,000;

(b) a diacid selected from the group consisting of HO(O)C—(CH$_2$)$_c$—C(O)OH, HO(O)C—(CH$_2$)$_d$—CH═CH—(CH$_2$)$_e$—C(O)OH and dimer acid; c, d and e are independently integers from 1 to 10; and (c) a fluorine containing hydroxy compound conforming to the following structure;

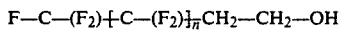

n is ranges from 3 to 17.

The compounds of the present invention conform to the following structure;

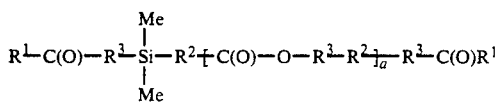

wherein

Me is methyl;

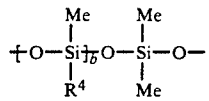

R$^1$ conforms to the following structure;

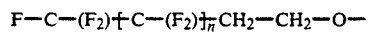

n is an integer ranging from 3 to 17;

R$^3$ is selected from the group consisting of —(CH$_2$)$_c$—C(O)—O—, —(CH$_2$)$_d$—CH═CH—(CH$_2$)$_e$—C(O)—O—; or the dimer acid residue;

a is an integer from 0 to 20;

b is an integer from 1 to 2,000;

c, d and e are independently integers from 1 to 10;

R$^4$ is alkyl having from 1 to 18 carbon units or phenyl.

Dimer acid is well known to those skilled in the art and are prepared by the thermal condensation of unsaturated fatty acids catalyzed by a small amount of montmorillonite clay are described in numerous patents by C. G. Gobel (U.S. Pat. Nos. 2,482,761, 2,793,219, 2,793,220, 2,955,121, 3,076,003 and 3,100,784), incorporated herein by reference. Basically, dimer acid is the Diels Alder reaction of unsaturated mono fatty acids containing 18 carbon atoms; to produce a 36 carbon diacid. There are basically three structures which result. They are;

| UNSATURATED SPECIES | |
|---|---|
| STRUCTURE | DESIGNATION |
| CH$_3$—(CH$_2$)$_8$—CH—(CH$_2$)$_7$—C(O)—OH<br>CH$_3$—(CH$_2$)$_7$—CH═C—(CH$_2$)$_7$—C(O)—OH | Acyclic |
| (monocyclic structure with (CH$_2$)$_8$—C(O)OH, (CH$_2$)$_8$—COOH, CH═CH—(CH$_2$)$_4$—CH$_3$, (CH$_2$)$_4$—CH$_3$ substituents) | Monocyclic |
| (bicyclic structure with (CH$_2$)$_7$—C(O)OH, C—(CH$_2$)$_7$—C(O)—OH, CH$_3$—(CH$_2$)$_4$—, (CH$_2$)$_4$—CH$_3$ substituents) | Bicyclic |

R$^2$ is

The compounds are then hydrogenated to remove the double bonds to give the following;

| HYDROGENATED SPECIES | |
|---|---|
| STRUCTURE | DESIGNATION |
| CH₃—(CH₂)₈—CH—(CH₂)₇—C(O)—OH<br>CH₃—(CH₂)₇—CH₂CH—(CH₂)₇—C(O)—OH | Acyclic |
| (monocyclic structure shown) | Monocyclic |
| (bicyclic structure shown) | Bicyclic |

The above structures both in the hydrogenated and unsaturated forms are collectively referred to as "dimer acid" and the derivatives are referred to as those derived from a dimer acid residue.

PREFERRED EMBODIMENTS

In a preferred embodiment the fluorine content in the polymer ranges from 5% to 30% by weight.

In another preferred embodiment the fluorine content in the polymer ranges from 10% to 25% by weight.

In a preferred embodiment the diacid is dimer acid. This results in a material with superior conditioning effects on hair and skin and better compatibility in many organic oils.

In another preferred embodiment the diacid is dodecanedioic acid.

In still another preferred embodiment, the silanol used has a molecular weight of between 1,000 MWU and 86,000 MWU.

In still another preferred embodiment, the silanol used has a molecular weight of between 1,000 MWU and 50,000 MWU.

In still another preferred embodiment, the silanol used has a molecular weight of between 1,000 MWU and 10,000 MWU.

EXAMPLES

The compounds of the present invention are prepared by the reaction of a silanol compound a diacid and a fluorine containing alcohol. Examples of suitable reactants are as follows;

| Reactants | | |
|---|---|---|
| Diacids | Formula | Molecular Weight |
| Adipic Acid | HO(O)C(CH2)₄C(O)OH | 130 |
| Succinic Acid | HO(O)C(CH2)₂C(O)OH | 102 |
| Dodecandioic Acid | HO(O)C(CH2)₁₀C(O)OH | 230 |
| Dimer Acid | See Above | 286 |

| -continued | | |
|---|---|---|
| Reactants | | |
| Diacids | Formula | Molecular Weight |
| Maleic Acid | HO(O)C—CH=CH—C(O)OH | 100 |

Silanol Compounds

Silanol compounds are well known and are marketed in the trade under many names. The compounds conform to the following generic structure;

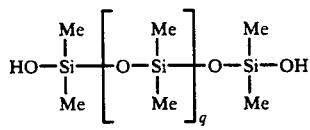

q is an integer ranging from 1 to 2,000.

The specific value of "q" for the commerical materials is easily calculated from the molecular weight. Compounds conforming to the above structure are available from Siltech Inc. Norcross Ga and are marketed under the Silteh S series tradename shown;

| Name | Molecular Weight |
|---|---|
| Siltech S 701 | 1,000 |
| Siltech S 706 | 6,000 |
| Siltech S 710 | 10,000 |
| Siltech S 750 | 50,000 |
| Siltech S 790 | 86,000 |

Fluorine Containing Alcohols

Fluorine containing alcohols are commercially available from a variety of suppliers, most importantly DuPonte Performance Products Division. They conform to the following structure;

F—C—(F$_2$)—[C—(F$_2$)]$_n$—CH$_2$—CH$_2$—OH n is ranges from 3 to 17.

| Reactant Example Number | n Value | Molecular Weight | % F |
|---|---|---|---|
| 1 | 3 | 264 | 64.7 |
| 2 | 5 | 364 | 67.8 |
| 3 | 7 | 464 | 69.6 |
| 4 | 9 | 564 | 70.7 |
| 5 | 11 | 664 | 71.5 |
| 6 | 13 | 764 | 72.1 |
| 7 | 15 | 864 | 72.5 |
| 8 | 17 | 964 | 72.9 |

Compounds of the Invention

The reaction can be run with varying amounts of fluorine containing alcohol. It should be clear that since only the fluorine containing material contains only one hydroxyl group it will be chain terminating. The other materials, namely the silanol and the diacid each have two functional groups.

Polymers of the following structure will result;

$$A + B - C +_s A$$

wherein;
A is the fluorine containing portion
B is the diacid
C is the silanol

The less amount of "A" used, the higher the "s" value, and the lower the fluorine content. That is because "A" is both a chain stopper and the fluorine source.

|  | "A" Concentration High | "A" Concentration Low |
|---|---|---|
| Molecular weight | Low | High |
| Fluorine Content | High | Low |
| "s" value | Low | High |

General Reaction Conditions

The esterification can be run without catalyst; however, when no catalysts used reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titanates, organo tin compounds, organo zinc compounds, zinc oxide, magnesium oxide, calcium oxide, etc.. The most preferred catalyst is stannous oxylate. The reaction is conducted at between 140 and 240 C. under an inert nitrogen blanket. The nitrogen blanket preserves the color. Preferred temperature range is between 180 and 210 C. Water is removed from the reaction which is done using a nitrogen sparge or vacuum.

EXAMPLES

General Procedure

Into a suitable round bottom, three neck flask equipped with a Dean Stark trap, a thermometer and a nitrogen sparge is added the specified number of grams of the diacid, the specified number of silanol, the specified number of grams of fluorine containing alcohol and 0.25% of total weight of the batch of catalyst. The reaction mass is blanketed with nitrogen, and heated to 180 and 200 C. under an inert nitrogen blanket. Once the reaction temperature reaches 120 C. water begins to boil off and is collected in the Dean Stark Trap. Within four to five hours the theoretical water is collected off and the acid value is very low. The product is a white wax and is used without additional purification.

EXAMPLE 9

Into a suitable round bottom, three neck flask equipped with a Dean Stark trap, a thermometer and a nitrogen sparge is added the specified number of 130.0 grams of the Adipic Acid (the diacid), the 500 grams of S-701 (Siltech S 701) (the silanol), 264.0 grams of Reactant Example 1, (the fluorine containing alcohol) and 0.25% of total weight of the batch of catalyst. The reaction mass is blanketed with nitrogen, and heated to 180 and 200 C. under an inert nitrogen blanket. Once the reaction temperature reaches 120 C. water begins to boil off and is collected in the Dean Stark Trap. Within four to five hours the theoretical water is collected off and the acid value is very low. The product is a white wax and is used without additional purification.

EXAMPLE 10—33

Example 9 is repeated only this time substituting the specified number of grams of the specified diacid for the dimer acid and the specified type and number of grams of silanol and the specified type and number of grams of fluorine containing compound as shown below;

Note; In the below table Gms. is grams and the silanol designation S 706 means Siltech S 706 as described above.

| Example | Diacid | "F" Alcohol | Silanol |
|---|---|---|---|
| 10 | Succinic Acid 102.0 Gms. | Reactant Example 2 364.0 Gms. | S 706 3,000.0 Gms. |
| 11 | Dodecanedioic Acid 230.0 Gms. | Reactant Example 3 464.0 Gms. | S 710 5,000.0 Gms. |
| 12 | Dimer Acid 286.0 Gms. | Reactant Example 4 564.0 Gms. | S 750 25,000.0 Gms. |
| 13 | Hydrogenated Dimer Acid 286.0 Gms. | Reactant Example 5 664.0 Gms. | S 790 43,000.0 Gms. |
| 14 | Maleic Acid 100.0 Gms. | Reactant Example 6 764.0 Gms. | S 701 500.0 Gms. |
| 15 | Adipic Acid 130.0 Gms. | Reactant Example 7 864.0 Gms. | S 710 5,000.0 Gms. |
| 16 | Succinic Acid 102.0 Gms. | Reactant Example 8 964.0 Gms. | S 750 25,000.0 Gms. |
| 17 | Dodecanedioic Acid 230.0 Gms. | Reactant Example 1 264.0 Gms. | S 790 43,000.0 Gms. |
| 18 | Dimer Acid 286.0 Gms. | Reactant Example 2 364.0 Gms. | S 701 500.0 Gms. |
| 19 | Hydrogenated Dimer Acid 286.0 Gms. | Reactant Example 3 464.0 Gms | S 706 3,000.0 Gms. |
| 20 | Maleic Acid 100.0 Gms. | Reactant Example 4 564.0 Gms. | S 710 5,000.0 Gms. |
| 21 | Adipic Acid 130.0 Gms. | Reactant Example 5 664.0 Gms. | S 750 25,000.0 Gms. |
| 22 | Succinic Acid 102.0 Gms. | Reactant Example 6 764.0 Gms. | S 790 43,000.0 Gms. |
| 23 | Dodecanedioic Acid 230.0 Gms. | Reactant Example 7 432.0 Gms. | S 701 750.0 Gms. |
| 24 | Dimer Acid 286.0 Gms. | Reactant Example 8 964.0 Gms. | S 706 1,500.0 Gms. |
| 26 | Hydrogenated | Reactant Example 1 | S 710 |

-continued

| Example | Diacid | "F" Alcohol | Silanol |
|---|---|---|---|
|  | Dimer Acid 286.0 Gms. | 133.0 Gms. | 10,000.0 Gms. |
| 27 | Maleic Acid 100.0 Gms. | Reactant Example 2 50.0 Gms. | S 750 30,000.0 Gms. |
| 28 | Adipic Acid 130.0 Gms. | Reactant Example 3 464.0 Gms. | S 790 40,000.0 Gms. |
| 29 | Succinic Acid 102.0 Gms. | Reactant Example 4 564.0 Gms. | S 701 1,000.0 Gms. |
| 30 | Dodecanedioic Acid 230.0 Gms. | Reactant Example 5 664.0 Gms. | S 706 3,000.0 Gms. |
| 31 | Dimer Acid 286.0 Gms. | Reactant Example 6 764.0 Gms. | S 710 5,000.0 Gms. |
| 32 | Hydrogenated Dimer Acid 286.0 Gms. | Reactant Example 7 864.0 Gms. | S 750 50,000.0 Gms. |
| 33 | Maleic Acid 100.0 Gms. | Reactant Example 8 96.4 Gms. | S 790 80,000.0 Gms. |

APPLICATIONS EXAMPLES

Lubrication

FRICTIONAL PROPERTIES

|  |  | LUBRICATION DATA[1] Coefficient of Friction FIBER/METAL | |
|---|---|---|---|
| PRODUCT | DESCRIPTION (70 F.) | 100 (m/min.) | 300 |
| Butyl Stearate | White Liquid | 0.17 | 0.21 |
| Tridecyl Stearate | Clear Liquid | 0.25 | 0.27 |
| Example 30 | White Wax | 0.06 | 0.01 |
| Example 21 | White Wax | 0.07 | 0.02 |
| Ditallowdimethyl benzalkonium chloride | Tan solid | 0.35 | 0.35 |
| Ditridecyl adipate | Clear Amber Liquid | 0.28 | 0.29 |
| Untreated Fiber |  | 0.98 | 1.01 |

[1]Rothchild F Meter, Fiber; 150 denier polyester, Temperature: 72 F., Relative humidity: 60%

As can be easily seen the compounds of the present invention are excellent lubricants.

Wet Comb Out Test

A laboratory test is conducted to screen the wet comb properties of a representative member of the family of novel compounds. Hair swatches are purchased from a supply of human hair from the same head. Each test swatch contains 7 grams of hair and is 11 inches in length. The hair is tied tightly 1 inch from one end with string. The swatch is pre-cleaned with a 3% solution of ammonium lauryl sulfate. Subsequently, the swatch is washed under running tap water. The hair is then squeezed out and while still damp dipped into a 200 ml solution of 0.2% active quaternary. Another rinse is made, then the swatch is blotted dry. The swatch is then treated by holding the hair swatch, combing the hair as rapidly as possible while alternating the side of the swatch combed. The time needed to get one smooth free stroke without tangling is recorded. Typical results for the standard quaternary compounds used in hair conditioning (stearyldimethylbenzyl ammonium chloride) range from 12-14 seconds.

| Rinse Conditioner (Wet Comb Out Test) | |
|---|---|
| Product | Time in Seconds |
| Example #20 | 11 |
| Example #22 | 13 |

| Rinse Conditioner (Wet Comb Out Test) | |
|---|---|
| Product | Time in Seconds |
| Stearyldimethylbenzyl ammonium chloride | 12 |

As can be seen, the compounds of the invention give significant conditioning properties to hair makes them prime candidates for cosmetic as well as textile and other related applications. The following examples are typical formulations which utilize the compounds of the present invention;

Furniture and Automotive Wax

The compounds of the present invention can be incorporated into wax formulations for furniture and automotive applications. Their high lubrication properties as well as their being solid at ambient temperatures makes them excellent wax bases. The property of liquification under pressure also contributes to the functionality.

What is claimed;

1. A fluorine containing silanol polyester compound which is prepared by the esterification reaction of;
(a) a silanol compound conforming to the following structure;

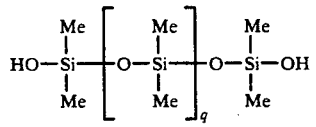

q is an integer ranging from 1 to 2,000;
(b) a diacid selected from the group consisting of HO(O)C—(CH$_2$)$_c$—C(O)OH, HO(O)C—(CH$_2$)$_d$—CH=CH—(CH$_2$)$_e$—C(O)OH and dimer acid;
c, d and e are independently integers from 1 to 10; and
(c) a fluorine containing hydroxy compound conforming to the following structure;

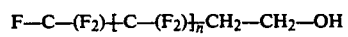

n is ranges from 3 to 17.

2. A compound of claim 1 wherein the fluorine content in the compound ranges from 5% to 30% by weight.

3. A compound of claim 1 wherein the fluorine content in the compound ranges from 10% to 25% by weight.

4. A compound of claim 1 wherein the diacid is dimer acid.

5. A compound of claim 1 wherein the diacid is dodecanedioic acid.

6. A compound of claim 1 wherein the silanol used has a molecular weight of between 1,000 MWU and 86,000 MWU.

7. A compound of claim 1 wherein the silanol used has a molecular weight of between 1,000 MWU and 50,000 MWU.

8. A compound of claim 1 wherein the silanol used has a molecular weight of between 1,000 MWU and 10,000 MWU.

9. A compound of claim 1 wherein n is 3.
10. A compound of claim 1 wherein n is 5.
11. A compound of claim 1 wherein n is 7.
12. A compound of claim 1 wherein n is 9.
13. A compound of claim 1 wherein n is 11.
14. A compound of claim 1 wherein n is 13.
15. A compound of claim 1 wherein n is 15.
16. A compound of claim 1 wherein n is 17.

* * * * *